(12) United States Patent
Yao et al.

(10) Patent No.: US 11,434,473 B2
(45) Date of Patent: Sep. 6, 2022

(54) GLUCOSE OXIDASE GOD MUTANT AND GENE AND APPLICATION THEREOF

(71) Applicant: INSTITUTE OF ANIMAL SCIENCE OF CHINESE ACADEMY OF AGRICULTURAL SCIENCES, Beijing (CN)

(72) Inventors: Bin Yao, Beijing (CN); Huiying Luo, Beijing (CN); Tao Tu, Beijing (CN); Huoqing Huang, Beijing (CN); Xiaoyun Su, Beijing (CN); Yaru Wang, Beijing (CN); Yingguo Bai, Beijing (CN); Yuan Wang, Beijing (CN); Kun Meng, Beijing (CN)

(*) Notice: Subject to any disclaimer, the term of this patent is extended or adjusted under 35 U.S.C. 154(b) by 0 days.

(21) Appl. No.: 15/734,568

(22) PCT Filed: Dec. 20, 2018

(86) PCT No.: PCT/CN2018/122270
§ 371 (c)(1),
(2) Date: Dec. 3, 2020

(87) PCT Pub. No.: WO2019/233083
PCT Pub. Date: Dec. 12, 2019

(65) Prior Publication Data
US 2021/0230561 A1 Jul. 29, 2021

(30) Foreign Application Priority Data
Jun. 4, 2018 (CN) .......................... 201810561796.6

(51) Int. Cl.
*C12N 9/04* (2006.01)

(52) U.S. Cl.
CPC .... *C12N 9/0006* (2013.01); *C12Y 101/03004* (2013.01)

(58) Field of Classification Search
None
See application file for complete search history.

(56) References Cited

U.S. PATENT DOCUMENTS 8,999,140 B2 * 4/2015 Kojima .................. C12Q 1/006
205/792

* cited by examiner

*Primary Examiner* — Richard G Hutson
(74) *Attorney, Agent, or Firm* — Patshegen IP; Moshe Pinchas

(57) ABSTRACT

The present invention takes the glucose oxidase GOD from *Aspergillus niger* as the mutation template to obtain the glucose oxidase GOD mutants with improved catalytic efficiency and thermal stability by site directed mutagenesis. The specific activity of the mutant of the present invention is 66% higher than that of the wild type GOD; the enzyme activity of the mutant of the present invention is 13.6 times higher than that of the wild type after being treated at 70° C. for 10 min; and the enzyme activity of the mutant of the present invention is 29.4 times higher than that of the wild type after being treated at 80° C. for 2 min.

7 Claims, 1 Drawing Sheet

Figure 1:
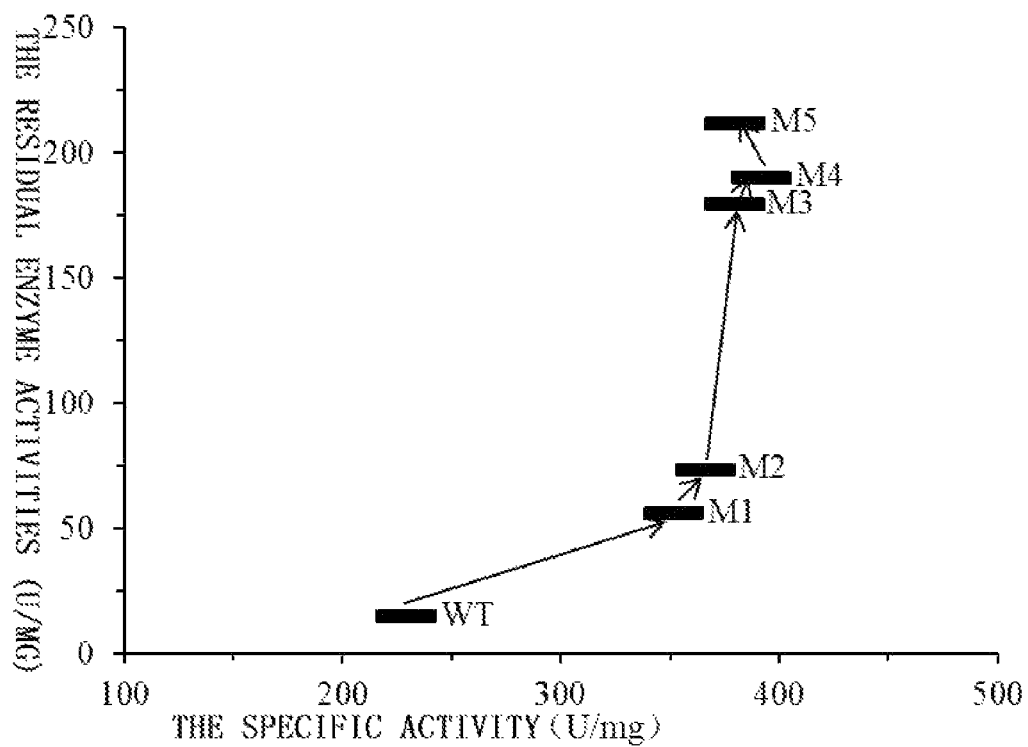

Specification includes a Sequence Listing.

SEQUENCE LISTING

<160> NUMBER OF SEQ ID NOS: 16

<210> SEQ ID NO 1
<211> LENGTH: 581
<212> TYPE: PRT
<213> ORGANISM: Aspergillus niger

<400> SEQUENCE: 1

```
Gly Ile Glu Ala Ser Leu Leu Thr Asp Pro Lys Glu Val Ala Gly Arg
1               5                  10                  15

Thr Val Asp Tyr Ile Ile Ala Gly Gly Gly Leu Thr Gly Leu Thr Thr
                20                  25                  30

Ala Ala Arg Leu Thr Glu Asn Pro Asp Ile Thr Val Leu Val Ile Glu
            35                  40                  45

Ser Gly Ser Tyr Glu Ser Asp Arg Gly Pro Ile Ile Glu Asp Leu Asn
    50                  55                  60

Ala Tyr Gly Asp Ile Phe Gly Ser Ser Val Asp His Ala Tyr Glu Thr
65                  70                  75                  80

Val Glu Leu Ala Thr Asn Asn Gln Thr Ala Leu Ile Arg Ser Gly Asn
                85                  90                  95

Gly Leu Gly Gly Ser Thr Leu Val Asn Gly Gly Thr Trp Thr Arg Pro
            100                 105                 110

His Lys Ala Gln Val Asp Ser Trp Glu Thr Val Phe Gly Asn Glu Gly
        115                 120                 125

Trp Asn Trp Asp Ser Val Ala Ala Tyr Ser Leu Gln Ala Glu Arg Ala
    130                 135                 140

Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
                165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
        195                 200                 205

Gly Val Ser Met Phe Pro Asn Thr Leu His Glu Asp Gln Val Arg Ser
    210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
                245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Leu Ala Ala Gly
        275                 280                 285

Ser Ala Val Ser Pro Thr Ile Leu Glu Tyr Ser Gly Ile Gly Met Lys
    290                 295                 300

Ser Ile Leu Glu Pro Leu Gly Ile Asp Thr Val Val Asp Leu Pro Val
305                 310                 315                 320

Gly Leu Asn Leu Gln Asp Gln Thr Thr Ser Thr Val Arg Ser Arg Ile
                325                 330                 335

Thr Ser Ala Gly Ala Gly Gln Gly Gln Ala Ala Trp Phe Ala Thr Phe
            340                 345                 350

Asn Glu Thr Phe Gly Asp Tyr Thr Glu Lys Ala His Glu Leu Leu Asn
        355                 360                 365
```

-continued

Thr Lys Leu Glu Gln Trp Ala Glu Glu Ala Val Ala Arg Gly Gly Phe
    370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
                405                 410                 415

Gly Val Ala Ser Phe Asp Val Trp Asp Leu Leu Pro Phe Thr Arg Gly
            420                 425                 430

Tyr Val His Ile Leu Asp Lys Asp Pro Tyr Leu Arg His Phe Ala Tyr
        435                 440                 445

Asp Pro Gln Tyr Phe Leu Asn Glu Leu Asp Leu Leu Gly Gln Ala Ala
    450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                485                 490                 495

Asp Leu Arg Ala Trp Val Glu Tyr Ile Pro Tyr Asn Phe Arg Pro Asn
            500                 505                 510

Tyr His Gly Val Gly Thr Cys Ser Met Met Pro Lys Glu Met Gly Gly
        515                 520                 525

Val Val Asp Asn Ala Ala Arg Val Tyr Gly Val Gln Gly Leu Arg Val
    530                 535                 540

Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Val Leu Ala Asp
                565                 570                 575

Tyr Ala Ser Met Gln
            580

<210> SEQ ID NO 2
<211> LENGTH: 581
<212> TYPE: PRT
<213> ORGANISM: Artificial Sequence
<220> FEATURE:
<223> OTHER INFORMATION: mutant

<400> SEQUENCE: 2

Gly Ile Glu Ala Ser Leu Leu Thr Asp Pro Lys Glu Val Ala Gly Arg
1               5                   10                  15

Thr Val Asp Tyr Ile Ile Ala Gly Gly Gly Leu Thr Gly Leu Thr Thr
                20                  25                  30

Ala Ala Arg Leu Thr Glu Asn Pro Asp Ile Thr Val Leu Val Ile Glu
            35                  40                  45

Ser Gly Ser Tyr Glu Ser Asp Arg Gly Pro Ile Ile Glu Asp Leu Asn
        50                  55                  60

Ala Tyr Gly Asp Ile Phe Gly Ser Ser Val Asp His Ala Tyr Glu Thr
65                  70                  75                  80

Val Cys Leu Ala Thr Asn Asn Gln Thr Ala Leu Ile Arg Ser Gly Asn
                85                  90                  95

Gly Leu Gly Gly Ser Thr Leu Val Asn Gly Gly Thr Trp Thr Arg Pro
            100                 105                 110

His Lys Ala Gln Val Asp Ser Trp Glu Thr Val Phe Gly Asn Glu Gly
        115                 120                 125

Trp Asn Trp Asp Ser Val Ala Ala Tyr Ser Leu Gln Ala Glu Arg Ala
    130                 135                 140

```
Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
            165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
        195                 200                 205

Gly Val Ser Met Phe Pro Asn Thr Leu His Glu Asp Gln Val Arg Ser
        210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
            245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Leu Ala Ala Gly
            275                 280                 285

Ser Ala Val Ser Pro Thr Ile Leu Glu Tyr Ser Gly Ile Gly Met Lys
290                 295                 300

Ser Ile Leu Glu Pro Leu Gly Ile Asp Thr Val Val Asp Leu Pro Val
305                 310                 315                 320

Gly Leu Asn Leu Gln Asp Gln Thr Thr Ser Thr Val Arg Ser Arg Ile
            325                 330                 335

Thr Ser Ala Gly Ala Gly Gln Gly Gln Ala Ala Trp Phe Ala Thr Phe
            340                 345                 350

Asn Glu Thr Phe Gly Asp Tyr Thr Glu Lys Ala His Glu Leu Leu Asn
            355                 360                 365

Thr Lys Leu Glu Gln Trp Ala Glu Glu Ala Val Ala Arg Gly Gly Phe
        370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
            405                 410                 415

Gly Val Ala Ser Phe Asp Val Trp Asp Leu Leu Pro Phe Thr Arg Gly
            420                 425                 430

Tyr Val His Ile Leu Asp Lys Asp Pro Tyr Leu Arg His Phe Ala Tyr
            435                 440                 445

Asp Pro Gln Tyr Phe Leu Asn Glu Leu Asp Leu Leu Gly Gln Ala Ala
        450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
            485                 490                 495

Asp Leu Arg Ala Trp Val Glu Tyr Ile Pro Tyr Asn Phe Arg Pro Asn
            500                 505                 510

Tyr His Gly Val Gly Thr Cys Ser Met Met Pro Lys Glu Met Gly Gly
            515                 520                 525

Val Val Asp Asn Ala Ala Arg Val Tyr Gly Val Gln Gly Leu Arg Val
        530                 535                 540

Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Val Leu Ala Asp
```

```
                        565                 570                 575

Tyr Ala Ser Met Gln
            580

<210> SEQ ID NO 3
<211> LENGTH: 581
<212> TYPE: PRT
<213> ORGANISM: Artificial Sequence
<220> FEATURE:
<223> OTHER INFORMATION: mutant

<400> SEQUENCE: 3

Gly Ile Glu Ala Ser Leu Leu Thr Asp Pro Lys Glu Val Ala Gly Arg
1               5                   10                  15

Thr Val Asp Tyr Ile Ile Ala Gly Gly Gly Leu Thr Gly Leu Thr Thr
            20                  25                  30

Ala Ala Arg Leu Thr Glu Asn Pro Asp Ile Thr Val Leu Val Ile Glu
        35                  40                  45

Ser Gly Ser Tyr Glu Ser Asp Arg Gly Pro Ile Ile Glu Asp Leu Asn
    50                  55                  60

Ala Tyr Gly Asp Ile Phe Gly Ser Ser Val Asp His Ala Tyr Glu Thr
65                  70                  75                  80

Val Cys Leu Ala Thr Asn Asn Gln Thr Ala Leu Ile Arg Ser Gly Asn
            85                  90                  95

Gly Leu Gly Gly Ser Thr Leu Val Asn Gly Gly Thr Trp Thr Arg Pro
            100                 105                 110

His Lys Ala Gln Val Asp Ser Trp Glu Thr Val Phe Gly Asn Glu Gly
        115                 120                 125

Trp Asn Trp Asp Ser Val Ala Ala Tyr Ser Leu Gln Ala Glu Arg Ala
    130                 135                 140

Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
                165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
        195                 200                 205

Gly Val Ser Met Phe Pro Asn Thr Leu His Glu Asp Gln Val Arg Ser
    210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
                245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Leu Ala Ala Gly
        275                 280                 285

Ser Ala Val Ser Pro Thr Ile Leu Glu Tyr Ser Gly Ile Gly Met Lys
    290                 295                 300

Ser Ile Leu Glu Pro Leu Gly Ile Asp Thr Val Val Asp Leu Pro Val
305                 310                 315                 320

Gly Leu Asn Leu Gln Asp Gln Thr Thr Ser Thr Val Arg Ser Arg Ile
                325                 330                 335

Thr Ser Ala Gly Ala Gly Gln Gly Gln Ala Ala Trp Phe Ala Thr Phe
```

-continued

```
                340                 345                 350
Asn Glu Thr Phe Gly Asp Tyr Thr Glu Lys Ala His Glu Leu Leu Asn
            355                 360                 365

Thr Lys Leu Glu Gln Trp Ala Glu Glu Ala Val Ala Arg Gly Gly Phe
        370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
                405                 410                 415

Gly Glu Ala Ser Phe Asp Val Trp Asp Leu Leu Pro Phe Thr Arg Gly
            420                 425                 430

Tyr Val His Ile Leu Asp Lys Asp Pro Tyr Leu Arg His Phe Ala Tyr
        435                 440                 445

Asp Pro Gln Tyr Phe Leu Asn Glu Leu Asp Leu Gly Gln Ala Ala
        450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                485                 490                 495

Asp Leu Arg Ala Trp Val Glu Tyr Ile Pro Tyr Asn Phe Arg Pro Asn
            500                 505                 510

Tyr His Gly Val Gly Thr Cys Ser Met Met Pro Lys Glu Met Gly Gly
        515                 520                 525

Val Val Asp Asn Ala Ala Arg Val Tyr Gly Val Gln Gly Leu Arg Val
    530                 535                 540

Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Val Leu Ala Asp
                565                 570                 575

Tyr Ala Ser Met Gln
            580

<210> SEQ ID NO 4
<211> LENGTH: 581
<212> TYPE: PRT
<213> ORGANISM: Artificial Sequence
<220> FEATURE:
<223> OTHER INFORMATION: mutant

<400> SEQUENCE: 4

Gly Ile Glu Ala Ser Leu Leu Thr Asp Pro Lys Glu Val Ala Gly Arg
1               5                   10                  15

Thr Val Asp Tyr Ile Ile Ala Gly Gly Gly Leu Thr Gly Leu Thr Thr
            20                  25                  30

Ala Ala Arg Leu Thr Glu Asn Pro Asp Ile Thr Val Leu Val Ile Glu
        35                  40                  45

Ser Gly Ser Tyr Glu Ser Asp Arg Gly Pro Ile Ile Glu Asp Leu Asn
    50                  55                  60

Ala Tyr Gly Asp Ile Phe Gly Ser Ser Val Asp His Ala Tyr Glu Thr
65                  70                  75                  80

Val Cys Leu Ala Thr Asn Asn Gln Thr Ala Leu Ile Arg Ser Gly Asn
                85                  90                  95

Gly Leu Gly Gly Ser Thr Leu Val Asn Gly Gly Thr Trp Thr Arg Pro
            100                 105                 110

His Lys Ala Gln Val Asp Ser Trp Glu Thr Val Phe Gly Asn Glu Gly
```

```
            115                 120                 125
Trp Asn Trp Asp Ser Val Ala Ala Tyr Ser Leu Gln Ala Glu Arg Ala
    130                 135                 140

Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
                165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
        195                 200                 205

Gly Val Ser Met Phe Pro Asn Thr Leu His Glu Asp Gln Val Arg Ser
    210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
                245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Leu Ala Ala Gly
        275                 280                 285

Ser Ala Val Ser Pro Thr Ile Leu Glu Tyr Ser Gly Ile Gly Met Lys
    290                 295                 300

Ser Ile Leu Glu Pro Leu Gly Ile Asp Thr Val Val Asp Leu Pro Val
305                 310                 315                 320

Gly Leu Asn Leu Gln Asp Gln Thr Thr Ser Thr Val Arg Ser Arg Ile
                325                 330                 335

Thr Ser Ala Gly Ala Gly Gln Gln Ala Ala Trp Phe Ala Thr Phe
            340                 345                 350

Asn Glu Thr Phe Gly Asp Tyr Thr Glu Lys Ala His Glu Leu Leu Asn
        355                 360                 365

Thr Lys Leu Glu Gln Trp Ala Glu Glu Ala Val Ala Arg Gly Gly Phe
    370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
                405                 410                 415

Gly Glu Ala Ser Phe Asp Val Trp Asp Leu Leu Pro Phe Thr Arg Gly
            420                 425                 430

Tyr Val His Ile Leu Asp Lys Asp Pro Tyr Leu Arg His Phe Ala Tyr
        435                 440                 445

Asp Pro Gln Tyr Phe Leu Asn Glu Leu Asp Leu Leu Gly Gln Ala Ala
    450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                485                 490                 495

Asp Leu Arg Ala Trp Val Glu Tyr Ile Pro Tyr His Phe Arg Pro Asn
            500                 505                 510

Tyr His Gly Val Gly Thr Cys Ser Met Met Pro Lys Glu Met Gly Gly
        515                 520                 525

Val Val Asp Asn Ala Ala Arg Val Tyr Gly Val Gln Gly Leu Arg Val
    530                 535                 540
```

```
Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Val Leu Ala Asp
                565                 570                 575

Tyr Ala Ser Met Gln
            580

<210> SEQ ID NO 5
<211> LENGTH: 581
<212> TYPE: PRT
<213> ORGANISM: Artificial Sequence
<220> FEATURE:
<223> OTHER INFORMATION: mutant

<400> SEQUENCE: 5

Gly Ile Glu Ala Ser Leu Leu Thr Asp Pro Lys Glu Val Ala Gly Arg
1               5                   10                  15

Thr Val Asp Tyr Ile Ile Ala Gly Gly Gly Leu Thr Gly Leu Thr Val
                20                  25                  30

Ala Ala Arg Leu Thr Glu Asn Pro Asp Ile Thr Val Leu Val Ile Glu
            35                  40                  45

Ser Gly Ser Tyr Glu Ser Asp Arg Gly Pro Ile Ile Glu Asp Leu Asn
50                  55                  60

Ala Tyr Gly Asp Ile Phe Gly Ser Ser Val Asp His Ala Tyr Glu Thr
65                  70                  75                  80

Val Cys Leu Ala Thr Asn Asn Gln Thr Ala Leu Ile Arg Ser Gly Asn
                85                  90                  95

Gly Leu Gly Gly Ser Thr Leu Val Asn Gly Gly Thr Trp Thr Arg Pro
            100                 105                 110

His Lys Ala Gln Val Asp Ser Trp Glu Thr Val Phe Gly Asn Glu Gly
            115                 120                 125

Trp Asn Trp Asp Ser Val Ala Ala Tyr Ser Leu Gln Ala Glu Arg Ala
            130                 135                 140

Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
                165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
            195                 200                 205

Gly Val Ser Met Phe Pro Asn Thr Leu His Glu Asp Gln Val Arg Ser
            210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
                245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Leu Ala Ala Gly
            275                 280                 285

Ser Ala Val Ser Pro Thr Ile Leu Glu Tyr Ser Gly Ile Gly Met Lys
            290                 295                 300

Ser Ile Leu Glu Pro Leu Gly Ile Asp Thr Val Val Asp Leu Pro Val
305                 310                 315                 320
```

```
Gly Leu Asn Leu Gln Asp Gln Thr Thr Ser Thr Val Arg Ser Arg Ile
            325                 330                 335

Thr Ser Ala Gly Ala Gly Gln Gly Gln Ala Ala Trp Phe Ala Thr Phe
            340                 345                 350

Asn Glu Thr Phe Gly Asp Tyr Thr Glu Lys Ala His Glu Leu Leu Asn
            355                 360                 365

Thr Lys Leu Glu Gln Trp Ala Glu Glu Ala Val Ala Arg Gly Gly Phe
            370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
                405                 410                 415

Gly Glu Ala Ser Phe Asp Val Trp Asp Leu Leu Pro Phe Thr Arg Gly
            420                 425                 430

Tyr Val His Ile Leu Asp Lys Asp Pro Tyr Leu Arg His Phe Ala Tyr
            435                 440                 445

Asp Pro Gln Tyr Phe Leu Asn Glu Leu Asp Leu Leu Gly Gln Ala Ala
            450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                485                 490                 495

Asp Leu Arg Ala Trp Val Glu Tyr Ile Pro Tyr His Phe Arg Pro Asn
            500                 505                 510

Tyr His Gly Val Gly Thr Cys Ser Met Met Pro Lys Glu Met Gly Gly
            515                 520                 525

Val Val Asp Asn Ala Ala Arg Val Tyr Gly Val Gln Gly Leu Arg Val
            530                 535                 540

Ile Asp Gly Ser Ile Pro Pro Thr Gln Met Ser Ser His Val Met Thr
545                 550                 555                 560

Val Phe Tyr Ala Met Ala Leu Lys Ile Ala Asp Ala Val Leu Ala Asp
                565                 570                 575

Tyr Ala Ser Met Gln
            580

<210> SEQ ID NO 6
<211> LENGTH: 581
<212> TYPE: PRT
<213> ORGANISM: Artificial Sequence
<220> FEATURE:
<223> OTHER INFORMATION: mutant

<400> SEQUENCE: 6

Gly Ile Glu Ala Ser Leu Leu Thr Asp Pro Lys Glu Val Ala Gly Arg
1               5                   10                  15

Thr Val Asp Tyr Ile Ile Ala Gly Gly Gly Leu Thr Gly Leu Thr Val
            20                  25                  30

Ala Ala Arg Leu Thr Glu Asn Pro Asp Ile Thr Val Leu Val Ile Glu
            35                  40                  45

Ser Gly Ser Tyr Glu Ser Asp Arg Gly Pro Ile Ile Glu Asp Leu Asn
        50                  55                  60

Ala Tyr Gly Asp Ile Phe Gly Ser Ser Val Asp His Ala Tyr Glu Thr
65                  70                  75                  80

Val Cys Leu Ala Thr Asn Asn Gln Thr Ala Leu Ile Arg Ser Gly Asn
                85                  90                  95
```

```
Gly Leu Gly Gly Ser Thr Leu Val Asn Gly Thr Trp Thr Arg Pro
            100                 105                 110

His Lys Ala Gln Val Asp Ser Trp Glu Thr Val Phe Gly Asn Glu Gly
            115                 120                 125

Trp Asn Trp Asp Ser Val Ala Ala Tyr Ser Leu Gln Ala Glu Arg Ala
130                 135                 140

Arg Ala Pro Asn Ala Lys Gln Ile Ala Ala Gly His Tyr Phe Asn Ala
145                 150                 155                 160

Ser Cys His Gly Ile Asn Gly Thr Val His Ala Gly Pro Arg Asp Thr
                165                 170                 175

Gly Asp Asp Tyr Ser Pro Ile Val Lys Ala Leu Met Ser Ala Val Glu
            180                 185                 190

Asp Arg Gly Val Pro Thr Lys Lys Asp Leu Gly Cys Gly Asp Pro His
            195                 200                 205

Gly Val Ser Met Phe Pro Asn Thr Leu His Glu Asp Gln Val Arg Ser
    210                 215                 220

Asp Ala Ala Arg Glu Trp Leu Leu Pro Asn Tyr Gln Arg Pro Asn Leu
225                 230                 235                 240

Gln Val Leu Thr Gly Gln Tyr Val Gly Lys Val Leu Leu Ser Gln Asn
                245                 250                 255

Ala Thr Thr Pro Arg Ala Val Gly Val Glu Phe Gly Thr His Lys Gly
            260                 265                 270

Asn Thr His Asn Val Tyr Ala Lys His Glu Val Leu Ala Ala Gly
            275                 280                 285

Ser Ala Val Ser Pro Thr Ile Leu Glu Tyr Ser Gly Ile Gly Met Lys
    290                 295                 300

Ser Ile Leu Glu Pro Leu Gly Ile Lys Thr Val Val Asp Leu Pro Val
305                 310                 315                 320

Gly Leu Asn Leu Gln Asp Gln Thr Thr Ser Thr Val Arg Ser Arg Ile
                325                 330                 335

Thr Ser Ala Gly Ala Gly Gln Gly Gln Ala Ala Trp Phe Ala Thr Phe
            340                 345                 350

Asn Glu Thr Phe Gly Asp Tyr Thr Glu Lys Ala His Glu Leu Leu Asn
            355                 360                 365

Thr Lys Leu Glu Gln Trp Ala Glu Glu Ala Val Ala Arg Gly Gly Phe
370                 375                 380

His Asn Thr Thr Ala Leu Leu Ile Gln Tyr Glu Asn Tyr Arg Asp Trp
385                 390                 395                 400

Ile Val Lys Asp Asn Val Ala Tyr Ser Glu Leu Phe Leu Asp Thr Ala
                405                 410                 415

Gly Glu Ala Ser Phe Asp Val Trp Asp Leu Leu Pro Phe Thr Arg Gly
            420                 425                 430

Tyr Val His Ile Leu Asp Lys Asp Pro Tyr Leu Arg His Phe Ala Tyr
            435                 440                 445

Asp Pro Gln Tyr Phe Leu Asn Glu Leu Asp Leu Leu Gly Gln Ala Ala
    450                 455                 460

Ala Thr Gln Leu Ala Arg Asn Ile Ser Asn Ser Gly Ala Met Gln Thr
465                 470                 475                 480

Tyr Phe Ala Gly Glu Thr Ile Pro Gly Asp Asn Leu Ala Tyr Asp Ala
                485                 490                 495

Asp Leu Arg Ala Trp Val Glu Tyr Ile Pro Tyr His Phe Arg Pro Asn
            500                 505                 510
```

-continued

```
        Tyr His Gly Val Gly Thr Cys Ser Met Met Pro Lys Glu Met Gly Gly
            515                 520                 525

Val Val Asp Asn Ala Ala Arg Val Tyr Gly Val Gln Gly Leu Arg Val
            530                 535                 540

Ile Asp Gly Ser Ile Pro Pro Thr Gln Met Ser Ser His Val Met Thr
        545                 550                 555                 560

Val Phe Tyr Ala Met Ala Leu Lys Ile Ala Asp Ala Val Leu Ala Asp
                        565                 570                 575

Tyr Ala Ser Met Gln
                    580

<210> SEQ ID NO 7
<211> LENGTH: 30
<212> TYPE: DNA
<213> ORGANISM: Artificial Sequence
<220> FEATURE:
<223> OTHER INFORMATION: synthesized primer

<400> SEQUENCE: 7
actggtttga ctgtcgctgc cagattgact                                          30

<210> SEQ ID NO 8
<211> LENGTH: 30
<212> TYPE: DNA
<213> ORGANISM: Artificial Sequence
<220> FEATURE:
<223> OTHER INFORMATION: synthesized primer

<400> SEQUENCE: 8
caatctggca gcgacagtca aaccagtcaa                                          30

<210> SEQ ID NO 9
<211> LENGTH: 30
<212> TYPE: DNA
<213> ORGANISM: Artificial Sequence
<220> FEATURE:
<223> OTHER INFORMATION: synthesized primer

<400> SEQUENCE: 9
tacgagactg tctgccttgc cactaacaat                                          30

<210> SEQ ID NO 10
<211> LENGTH: 30
<212> TYPE: DNA
<213> ORGANISM: Artificial Sequence
<220> FEATURE:
<223> OTHER INFORMATION: synthesized primer

<400> SEQUENCE: 10
gttagtggca aggcagacag tctcgtaagc                                          30

<210> SEQ ID NO 11
<211> LENGTH: 30
<212> TYPE: DNA
<213> ORGANISM: Artificial Sequence
<220> FEATURE:
<223> OTHER INFORMATION: synthesized primer

<400> SEQUENCE: 11
ccacttggta ttaagaccgt cgttgacttg                                          30

<210> SEQ ID NO 12
<211> LENGTH: 30
<212> TYPE: DNA
```

```
<213> ORGANISM: Artificial Sequence
<220> FEATURE:
<223> OTHER INFORMATION: synthesized primer

<400> SEQUENCE: 12
gtcaacgacg gtcttaatac caagtggttc                                           30

<210> SEQ ID NO 13
<211> LENGTH: 30
<212> TYPE: DNA
<213> ORGANISM: Artificial Sequence
<220> FEATURE:
<223> OTHER INFORMATION: synthesized primer

<400> SEQUENCE: 13
gacactgccg gtgaggcttc cttcgacgtc                                           30

<210> SEQ ID NO 14
<211> LENGTH: 30
<212> TYPE: DNA
<213> ORGANISM: Artificial Sequence
<220> FEATURE:
<223> OTHER INFORMATION: synthesized primer

<400> SEQUENCE: 14
gtcgaaggaa gcctcaccgg cagtgtccaa                                           30

<210> SEQ ID NO 15
<211> LENGTH: 30
<212> TYPE: DNA
<213> ORGANISM: Artificial Sequence
<220> FEATURE:
<223> OTHER INFORMATION: synthesized primer

<400> SEQUENCE: 15
tacattccat accacttcag acctaactac                                           30

<210> SEQ ID NO 16
<211> LENGTH: 30
<212> TYPE: DNA
<213> ORGANISM: Artificial Sequence
<220> FEATURE:
<223> OTHER INFORMATION: synthesized primer

<400> SEQUENCE: 16
gttaggtctg aagtggtatg gaatgtattc                                           30
```

GLUCOSE OXIDASE GOD MUTANT AND GENE AND APPLICATION THEREOF

FIELD OF THE INVENTION

The present invention relates to the field of genetic engineering, particularly to a glucose oxidase GOD mutant, gene and application thereof.

BACKGROUND OF THE INVENTION

Glucose oxidase (GOD) is a flavin protein, which can highly specifically oxidize β-D-glucose into gluconolactone and hydrogen peroxide with dioxygen as electron acceptor, so it is also called aerobic dehydrogenase. The catalytic reaction can be divided into two processes of reduction reaction that GOD oxidizes β-D-glucose into gluconolactone being converted into gluconic acid in non-enzymatic reaction, and the cofactor flavin adenine dinucleotide (FAD) of GOD is reduced to FADH2, and oxidation reaction that the reducible GOD-FADH2 is reoxidized into GOD-FAD by reacting with dioxygen, and $H_2O_2$ is generated. GOD is widely used in the fields of chemistry, pharmacy, food, clinical diagnosis, biotechnology and so on. Especially, in the field of animal husbandry, the emergence of GOD has changed the traditional prevention and health care mode of livestock and poultry only against pathogen germs. Based on the characteristics of consuming oxygen and producing gluconic acid and hydrogen peroxide in the reaction process, GOD has the intestine physiological functions of protecting the integrity of intestinal epithelial cells, improving the intestinal acidic digestion environment, controlling the growth and reproduction of intestinal bacteria, maintaining the ecological balance of intestinal flora and preventing from intestinal mycotoxin poisoning.

At present, the GOD is industrially produced mainly from *Aspergillus niger* and *Penicillium*, but the yield of GOD was low, which could be significantly increased by heterologous expression. However, the application of GOD requires the higher thermal stability and catalytic activity.

ORDER OF THE INVENTION

In order to solve the problem of improving thermal stability and catalytic activity of the prior glucose oxidase, the present invention provides glucose oxidase mutants GOD-M1, GOD-M2, GOD-M3, GOD-M4 and GOD-M5 having higher thermal stability and enzyme activity than those of the wild glucose oxidase.

The order of the present invention is to provide a glucose oxidase GOD mutant.

Another order of the present invention is to provide genes encoding the above glucose oxidase GOD mutant.

Another order of the present invention is to provide a recombinant vector containing the glucose oxidase GOD mutant gene.

Another order of the present invention is to provide a recombinant strain containing the above glucose oxidase GOD mutant gene.

Another order of the present invention is to provide a genetic engineering method for preparing the glucose oxidase GOD mutant.

Another order of the present invention is to provide application of the above glucose oxidase GOD mutant.

SUMMARY OF THE INVENTION

In a preferred embodiment of the present invention, the amino acid sequence of the wild-type glucose oxidase GOD is shown in SEQ ID No: 1.

SEQ ID No: 1
GIEASLLTDPKEVAGRTVDYIIAGGGLTGLTTAARLTENPDITVL

VIESGSYESDRGPIIEDLNAYGDIFGSSVDHAYETVELATNNQTA

LIRSGNGLGGSTLVNGGTWTRPHKAQVDSWETVFGNEGWNWDSVA

AYSLQAERARAPNAKQIAAGHYFNASCHGINGTVHAGPRDTGDDY

SPIVKALMSAVEDRGVPTKKDLGCGDPHGVSMFPNTLHEDQVRSD

AAREWLLPNYQRPNLQVLTGQYVGKVLLSQNATTPRAVGVEFGTH

KGNTHNVYAKHEVLLAAGSAVSPTILEYSGIGMKSILEPLGIDTV

VDLPVGLNLQDQTTSTVRSRITSAGAGQGQAAWFATFNETFGDYT

EKAHELLNTKLEQWAEEAVARGGFHNTTALLIQYENYRDWIVKDN

VAYSELFLDTAGVASFDVWDLLPFTRGYVHILDKDPYLRHFAYDP

QYFLNELDLLGQAAATQLARNISNSGAMQTYFAGETIPGDNLAYD

ADLRAWVEYIPYNFRPNYHGVGTCSMMPKEMGGVVDNAARVYGVQ

GLRVIDGSIPPTQMSSHVMTVFYAMALKIADAVLADYASMQ*

In a yet preferred embodiment of the present invention, Glu at the $82^{nd}$ position of the amino acid sequence of the wild-type glucose oxidase GOD is substituted with Cys to obtain the glucose oxidase mutant GOD-M1.

In a further preferred embodiment, the amino acid sequence of the glucose oxidase mutant GOD-M1 is shown in SEQ ID No: 2.

SEQ ID No: 2
GIEASLLTDPKEVAGRTVDYIIAGGGLTGLTTAARLTENPDITVL

VIESGSYESDRGPIIEDLNAYGDIFGSSVDHAYETV<u>C</u>LATNNQTA

LIRSGNGLGGSTLVNGGTWTRPHKAQVDSWETVFGNEGWNWDSVA

AYSLQAERARAPNAKQIAAGHYFNASCHGINGTVHAGPRDTGDDY

SPIVKALMSAVEDRGVPTKKDLGCGDPHGVSMFPNTLHEDQVRSD

AAREWLLPNYQRPNLQVLTGQYVGKVLLSQNATTPRAVGVEFGTH

KGNTHNVYAKHEVLLAAGSAVSPTILEYSGIGMKSILEPLGIDTV

VDLPVGLNLQDQTTSTVRSRITSAGAGQGQAAWFATFNETFGDYT

EKAHELLNTKLEQWAEEAVARGGFHNTTALLIQYENYRDWIVKDN

VAYSELFLDTAGVASFDVWDLLPFTRGYVHILDKDPYLRHFAYDP

QYFLNELDLLGQAAATQLARNISNSGAMQTYFAGETIPGDNLAYD

ADLRAWVEYIPYNFRPNYHGVGTCSMMPKEMGGVVDNAARVYGVQ

GLRVIDGSIPPTQMSSHVMTVFYAMALKIADAVLADYASMQ*

In a yet preferred embodiment of the present invention, the mutation can be further performed to the amino acids at the sites of 418, 508, 32 and/or 313 of the glucose oxidase GOD.

In a further preferred embodiment, the amino acid Val at the $418^{th}$ position of the mutant GOD-M1 is substituted by the amino acid Glu to obtain the mutant GOD-M2, the amino acid Asn at the $508^{th}$ position of the mutant GOD-M2 is substituted by the amino acid His to obtain the mutant GOD-M3, the amino acid Thr at the $32^{nd}$ position of the mutant GOD-M3 is substituted by the amino acid Val to obtain the mutant GOD-M4, and the amino acid Asp at position 313 of GOD-M4 is substituted by the amino acid Lys to obtain the mutant GOD-M5.

In a further preferred embodiment, the amino acid sequence of the glucose oxidase mutant GOD-M2 is shown in SEQ ID No:3.

SEQ ID No: 3
GIEASLLTDPKEVAGRTVDYIIAGGGLTGLTTAARLTENPDITVLV

IESGSYESDRGPIIEDLNAYGDIFGSSVDHAYETVCLATNNQTALI

RSGNGLGGSTLVNGGTWTRPHKAQVDSWETVFGNEGWNWDSVAAYS

LQAERARAPNAKQIAAGHYFNASCHGINGTVHAGPRDTGDDYSPIV

KALMSAVEDRGVPTKKDLGCGDPHGVSMFPNTLHEDQVRSDAAREW

LLPNYQRPNLQVLTGQYVGKVLLSQNATTPRAVGVEFGTHKGNTHN

VYAKHEVLLAAGSAVSPTILEYSGIGMKSILEPLGIDTVVDLPVGL

NLQDQTTSTVRSRITSAGAGQGQAAWFATFNETFGDYTEKAHELLN

TKLEQWAEEAVARGGFHNTTALLIQYENYRDWIVKDNVAYSELFLD

TAGEASFDVWDLLPFTRGYVHILDKDPYLRHFAYDPQYFLNELDLL

GQAAATQLARNISNSGAMQTYFAGETIPGDNLAYDADLRAWVEYIP

YNFRPNYHGVGTCSMMPKEMGGVVDNAARVYGVQGLRVIDGSIPPT

QMSSHVMTVFYAMALKIADAVLADYASMQ*

In a further preferred embodiment, the amino acid sequence of the glucose oxidase mutant GOD-M3 is shown in SEQ ID No:4.

SEQ ID No: 4
GIEASLLTDPKEVAGRTVDYIIAGGGLTGLTTAARLTENPDITVL

VIESGSYESDRGPIIEDLNAYGDIFGSSVDHAYETVCLATNNQTA

LIRSGNGLGGSTLVNGGTWTRPHKAQVDSWETVFGNEGWNWDSVA

AYSLQAERARAPNAKQIAAGHYFNASCHGINGTVHAGPRDTGDDY

SPIVKALMSAVEDRGVPTKKDLGCGDPHGVSMFPNTLHEDQVRSD

AAREWLLPNYQRPNLQVLTGQYVGKVLLSQNATTPRAVGVEFGTH

KGNTHNVYAKHEVLLAAGSAVSPTILEYSGIGMKSILEPLGIDTV

VDLPVGLNLQDQTTSTVRSRITSAGAGQGQAAWFATFNETFGDYT

EKAHELLNTKLEQWAEEAVARGGFHNTTALLIQYENYRDWIVKDN

VAYSELFLDTAGEASFDVWDLLPFTRGYVHILDKDPYLRHFAYDP

QYFLNELDLLGQAAATQLARNISNSGAMQTYFAGETIPGDNLAYD

ADLRAWVEYIPYHFRPNYHGVGTCSMMPKEMGGVVDNAARVYGVQ

GLRVIDGSIPPTQMSSHVMTVFYAMALKIADAVLADYASMQ*

In a further preferred embodiment, the amino acid sequence of the glucose oxidase mutant GOD-M4 is shown in SEQ ID No:5.

SEQ ID No: 5
GIEASLLTDPKEVAGRTVDYIIAGGGLTGLTVAARLTENPDITVL

VIESGSYESDRGPIIEDLNAYGDIFGSSVDHAYETVCLATNNQTA

LIRSGNGLGGSTLVNGGTWTRPHKAQVDSWETVFGNEGWNWDSVA

AYSLQAERARAPNAKQIAAGHYFNASCHGINGTVHAGPRDTGDDY

SPIVKALMSAVEDRGVPTKKDLGCGDPHGVSMFPNTLHEDQVRSD

AAREWLLPNYQRPNLQVLTGQYVGKVLLSQNATTPRAVGVEFGTH

KGNTHNVYAKHEVLLAAGSAVSPTILEYSGIGMKSILEPLGIDTV

VDLPVGLNLQDQTTSTVRSRITSAGAGQGQAAWFATFNETFGDYT

EKAHELLNTKLEQWAEEAVARGGFHNTTALLIQYENYRDWIVKDN

VAYSELFLDTAGEASFDVWDLLPFTRGYVHILDKDPYLRHFAYDP

QYFLNELDLLGQAAATQLARNISNSGAMQTYFAGETIPGDNLAYD

ADLRAWVEYIPYHFRPNYHGVGTCSMMPKEMGGVVDNAARVYGVQ

GLRVIDGSIPPTQMSSHVMTVFYAMALKIADAVLADYASMQ*

In a further preferred embodiment, the amino acid sequence of the glucose oxidase mutant GOD-M5 is shown in SEQ ID No:6.

SEQ ID No:6
GIEASLLTDPKEVAGRTVDYIIAGGGLTGLTVAARLTENPDITVL

VIESGSYESDRGPIIEDLNAYGDIFGSSVDHAYETVCLATNNQTA

LIRSGNGLGGSTLVNGGTWTRPHKAQVDSWETVFGNEGWNWDSVA

AYSLQAERARAPNAKQIAAGHYFNASCHGINGTVHAGPRDTGDDY

SPIVKALMSAVEDRGVPTKKDLGCGDPHGVSMFPNTLHEDQVRSD

AAREWLLPNYQRPNLQVLTGQYVGKVLLSQNATTPRAVGVEFGTH

KGNTHNVYAKHEVLLAAGSAVSPTILEYSGIGMKSILEPLGIKTV

VDLPVGLNLQDQTTSTVRSRITSAGAGQGQAAWFATFNETFGDYT

EKAHELLNTKLEQWAEEAVARGGFHNTTALLIQYENYRDWIVKDN

VAYSELFLDTAGEASFDVWDLLPFTRGYVHILDKDPYLRHFAYDP

QYFLNELDLLGQAAATQLARNISNSGAMQTYFAGETIPGDNLAYD

ADLRAWVEYIPYHFRPNYHGVGTCSMMPKEMGGVVDNAARVYGVQ

GLRVIDGSIPPTQMSSHVMTVFYAMALKIADAVLADYASMQ*.

In a yet preferred embodiment of the present invention, the glucose oxidase GOD mutant is the mutant obtained by substitution, deletion and/or insertion of one or more, e.g., 1, 2, 3, 4, 5, 6, 7, 8 or 9, amino acid residues of any polypeptide of SEQ ID NO.2 to SEQ ID No.6, and maintaining the enzyme activity of the above glucose oxidase mutant.

For example, a common strategy is substitutions of the conservative amino acid that the amino acid residue is replaced with another amino acid residue having a similar side chain without effect on the properties of the enzyme. Families of amino acid residues having similar side chains have been defined in the art. Therefore, one or more amino acid sites of the glucose oxidase GOD mutant of the present invention are replaced by another amino acid residue from the same side chain class, which will not substantially affect the enzyme activity of the mutant. Furthermore, it is well known in the art that the suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions of the proteins, in order to construct a fusion protein, to enhance expression of recombinant protein, to obtain an recombinant protein automatically secreted outside the host cell, or to aid in the purification of the recombinant protein.

The invention provides a gene encoding the above glucose oxidase GOD mutant.

In a further preferred embodiment, the present invention provides the glucose oxidase GOD mutant gene having a nucleotide sequence which hybridizes to a nucleotide sequence encoding the polypeptide of SEQ ID No.2 to SEQ ID No.6 under stringent conditions. As used here, the term "hybridize under stringent condition" refers to the hybridization and cleaning conditions in which at least 75% of homologous nucleotide sequences can still be hybridized with each other. The said stringent condition are well known to those skilled in the art and can be found in current protocols in molecular biology, John Wiley & Sons, N.Y. (1989), 6.3.1-6.3.6. One example of hybridization under stringent conditions is hybridization in 6×SSC at 45° C., then washing one or more times at 50-65° C. in 0.2×SSc and 0.1% SDS. Those skilled in the art can understand that highly stringent conditions can be achieved by increasing the hybridization temperature, for example, to 50° C., 55° C., 60° C. or 65° C.

In addition, those skilled in the art will understand that there may exist the genetic polymorphism due to natural variation among individuals of a population.

The gene encoding the glucose oxidase GOD mutant of the present invention may have such natural variation without changing the activity of the mutant. Therefore, the present invention also includes the alleles of the genes encoding the polypeptide with amino acid sequence shown in SEQ ID No.2 to SEQ ID No.6 and the polypeptides with glucose oxidase mutant activity encoded by the natural variant.

The present invention provides recombinant vector comprising the gene encoding the abovementioned glucose oxidase GOD. The recombinant expression vectors of the invention can be designed for expressing glucose oxidase mutant protein in prokaryotic or eukaryotic cells. For example, glucose oxidase mutant gene can be expressed in bacterial cells such as *E. coli*, yeast such as *Pichia* or *Aspergillus*, insect cells such as Sf9 cell or silkworm cell with baculovirus expression vectors, or plant cell such as Arabidopsis, tobacco, corn, and so on, mediated by *Agrobacterium tumefaciens*.

Thus, the invention relates to host cells introduced with a recombinant expression vector of the invention. The host cells of the present invention may be any prokaryotic or eukaryotic cell, including but not limited to the above host cells. Preferably, said host cell is *Pichia* preferred. *Pichia pastoris* is methylotrophic yeast, capable of metabolizing methanol as its sole carbon source. This system is well-known for its ability to express high levels of heterologous proteins. As an effective expression system, many of the gene encoding the glucose oxidase have successfully expressed in *P. pastoris*. The novel gene encoding the mutant glucose oxidase of the present invention is also expressed in *P. pastoris* with high levels. So it will be very easy to mass-produce the glucose oxidase mutant by fermentation in the lower cost than ever.

The vector DNA can be transferred into prokaryotic or eukaryotic cells by the conventional transformation or transfection methods. Appropriate methods for transforming or transfecting host cells can be found in the second edition of *Molecular cloning* (Sambrook et al.), and other laboratory manuals.

The present invention provides a recombinant strain comprising the above gene encoding the glucose oxidase GOD mutant. Preferably, said recombinant strain is *Ecoli.*, yeast such as *Pichiapastoris cell, Saccharomyces cerevisiae*, or *Hansenulapolymorpha, Bacillus* or *Lactobacillus*, more preferably the recombinant *Pichia pastoris* strains GS115/GOD-M1, GS115/GOD-M2, GS115/GOD-M3, GS115/GOD-M4, GS115/GOD-M5.

In a further preferred embodiment, the preparation method of glucose oxidase GOD with the improved thermal stability and catalytic activity comprises the following steps of transforming the host cells with the recombinant vector containing the gene encoding the above glucose oxidase GOD mutant to obtain the recombinant strain, culturing the obtained recombinant strain to induce the expression of recombinant glucose oxidase GOD mutant, and recovering and purifying the glucose oxidase GOD.

The enzyme activity of the wild-type glucose oxidase GOD is 229.6 U/mg, and the enzyme activities of the mutants GOD-M1, GOD-M2, GOD-M3, GOD-M4 and GOD-M5 are increased to 352.5 U/mg, 366.8 U/mg, 379.8 U/mg, 392.1 U/mg, 381.2 U/mg, respectively, with the increase rate of 54%, 59.8%, 65.4%, 70.8% and 66%, respectively.

After being treated at 70° C. for 10 min, the residual enzyme activities of wild-type glucose oxidase GOD are 14.5 U/mg, and the residual enzyme activity of mutants GOD-M1, GOD-M2, GOD-M3, GOD-M4 and GOD-M5 is 55.9 U/mg, 73.1 U/mg, 179.2 U/mg, 189.8 U/mg, 211.2 U/mg, respectively, increasing 2.6, 4.0, 11.4, 12.1 and 13.6 times, respectively.

After treated at 80° C. for 2 min, the residual enzyme activity of the wild-type GOD is 4.5 U/mg, and the residual enzyme activities of the mutants GOD-M1, GOD-M2, GOD-M3, GOD-M4 and GOD-M5 are 23.6 U/mg, 35.5 U/mg g, 98.6 U/mg, 117.2 U/mg, 137.0 U/mg, respectively, increasing 4.2, 6.9, 20.9, 25.0, 29.4 times, respectively.

The present invention provides a glucose oxidase GOD mutant with high enzyme activity and improved thermal stability, which is suited well to meet the requirements of application to the fields of food, medicine, feed and textile industry, and has a very broad application prospect.

BRIEF DESCRIPTIONS OF THE DRAWINGS

Figure 2:
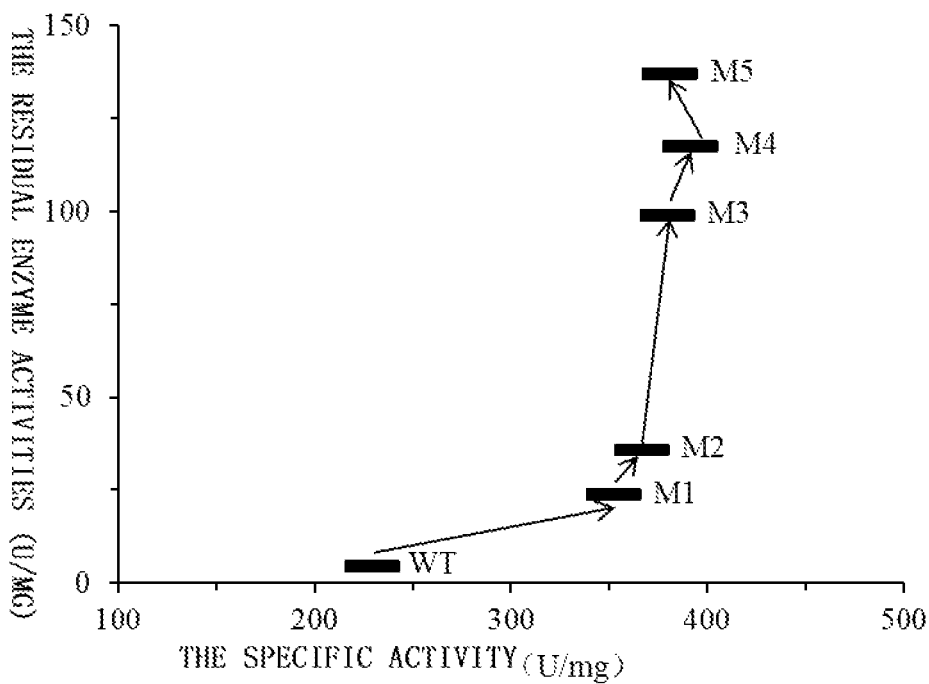

FIG. 1 shows the thermal stability of the wild type glucose oxidase and the mutants at 70° C. for 10 min, and FIG. 2 shows the thermal stability of the wild type glucose oxidase and the mutants at 80° C. for 2 min.

EMBODIMENT

Test Materials and Reagents

1. Strains and vectors: host: *Pichia pastoris* GS115; and vector pPIC9.

2. Enzymes and other biochemical reagents: point mutation kit and other biochemical reagents were purchased by biochemical reagent company.

3. Medium:

LB medium: 5% yeast extract, 1% peptone, 1% NaCL, pH 7.0;

YPD medium: 1% yeast extract, 2% peptone, 2% glucose;

MD solid medium: 2% glucose, 1.5% agarose, 1.34% YNB, 0.00004% Biotin;

MM solid medium: 1.5% agarose, 1.34% YNB, 0.00004% Biotin, 0.5% methanol;

BMGY medium: 1% yeast extract, 2% peptone, 1% glycerol (V/V), 1.34% YNB, 0.00004% Biotin;

BMMY medium: 1% yeast extract, 2% peptone, 1.34% YNB, 0.00004% Biotin, 0.5% methanol (V/V).

Example 1 Site Directed Mutagenesis

The glucose oxidase GOD having the acid sequence of SEQ ID No:1 from *Aspergillus niger* was performed the substation of the $82^{nd}$ amino acid Glu with the amino acid Cys to obtain the mutant GOD-M1; the amino acid Val at the site of 418 of GOD-M1 was substituted by the amino acid Glu to obtain the mutant GOD-M2; the $508^{th}$ amino acid Asn of GOD-M2 was substituted by the amino acid His to obtain the mutant GOD-M3; the amino acid Thr at the $32^{nd}$ position of GOD-M3 was substituted by the amino acid Val to obtain the mutant GOD-M4; the amino acid Asp at the site of 313 of GOD-M4 was substituted by the amino acid Lys to obtain the mutant GOD-M5.

The mutation sites were introduced by site directed mutagenesis PCR and verified by sequencing. The primers for PCR were shown in Table 1:

TABLE 1

The mutant specific primers

| Primers | Sequences (5'→3')$^a$ | Size (bp) |
|---|---|---|
| T32V-F | ACTGGTTTGACTGTCGCTGCCAGATTGACT | 30 |
| T32V-R | CAATCTGGCAGCGACAGTCAAACCAGTCAA | 30 |
| E82C-F | TACGAGACTGTCTGCCTTGCCACTAACAAT | 30 |
| E82C-R | GTTAGTGGCAAGGCAGACAGTCTCGTAAGC | 30 |
| D313K-F | CCACTTGGTATTAAGACCGTCGTTGACTTG | 30 |
| D313K-R | GTCAACGACGGTCTTAATACCAAGTGGTTC | 30 |
| V418E-F | GACACTGCCGGTGAGGCTTCCTTCGACGTC | 30 |
| V418E-R | GTCGAAGGAAGCCTCACCGGCAGTGTCCAA | 30 |
| N508H-F | TACATTCCATACCACTTCAGACCTAACTAC | 30 |
| N508H-R | GTTAGGTCTGAAGTGGTATGGAATGTATTC | 30 |

Example 2 Preparation of Glucose Oxidase GOD Mutant

The PCR products were added with 1 μL DMT enzyme and incubated at 37° C. for 1 h. 2-5 μL of DMT digestion products was transformed into competent cells by heat-shocking, followed by sequencing. And the recombinant plasmids containing the mutant gene were transformed into *Pichia pastoris* GS115 competent cells to obtain recombinant yeast strains GS115/GOD-M1, GS115/GOD-M2, GS115/GOD-M3, GS115/GOD-M4, and GS115/GOD-M5 respectively.

GS115 strain containing recombinant plasmid was inoculated into 300 mL of BMGY medium and incubated for 48 h at 30° C. and 220 rpm, followed by centrifuging at 3000 g for 5 min to remove the supernatant. The obtained precipitate was suspended in 100 mL of BMMY medium containing 0.5% of methanol to induce at 30° C. and 220 rpm with addition of 0.5 mL of methanol every 12 h to keep the concentration of methanol in the bacterial solution as 0.5%. After induction, the supernatant was recovered by spinning to test the activity of the enzyme Example 3 Analysis of the Activity of Glucose Oxidase GOD Mutant and Wild-Type Glucose Oxidase I. Determining the Activity of the Glucose Oxidase GOD with o-Anisidine The enzyme activity was determined by mixing 2.5 mL of o-anisidine buffer prepared by adding 0.2 mL of 1% o-anisidine to 25 mL of phosphate buffer in 0.1 M, 300 μL of 18% of glucose solution, 100 μL of 0.03% of horseradish peroxidase, and 100 μL of appropriate diluted release enzyme solution at pH6.0 to react for 3 min at 30° C., followed by adding 2 ml of $H_2SO_4$ in 2M to terminate the reaction and measuring the absorbance value at 540 nm. A unit of enzyme activity (U) is defined as the amount of enzyme required to produce 1 μmol gluconic acid and hydrogen peroxide per unit time under given conditions.

II. Measuring the Enzyme Activity and Thermal Stability of Glucose Oxidase GOD Mutant and Wild-Type Glucose Oxidase 1. Determining the Enzyme Activity of Glucose Oxidase GOD Mutant and Wild Type The enzyme activities of the glucose oxidase GOD mutant purified in example 2 and the wild-type glucose oxidase GOD were determined by performing the enzymatic reaction at pH 6.0 and 30° C.

The specific activity of the wild-type glucose oxidase GOD was 29.6 U/mg, and the activities of the mutants GOD-M1, GOD-M2, GOD-M3, GOD-M4 and GOD-M5 were increased to 352.5 U/mg, 366.8 U/mg, 379.8 U/mg, 392.1 U/mg, and 381.2 U/mg, respectively, with the increase rates of 54%, 59.8%, 65.4%, 70.8% and 66%, respectively.

2. Measuring the Thermal Stability of the Mutant and Wild-Type Glucose Oxidase GOD at 70° C. or 80° C.

the mutant glucose oxidase GOD and wild-type glucose oxidase GOD were treated at 70° C. for 10 min and 80° C. for 2 min in 0.1 mol/L of citric acid disodium hydrogen phosphate buffer (pH 6.0), respectively, followed by measuring the residual enzyme activity at 30° C.

As shown in FIG. 1, the residual enzyme activity of wild-type glucose oxidase GOD was 14.5 U/mg, and the residual enzyme activities of glucose oxidase mutants GOD-M1, GOD-M2, GOD-M3, GOD-M4 and GOD-M5 were 55.9 U/mg, 73.1 U/mg, 179.2 U/mg, 189.8 U/mg, 211.2 U/mg, respectively, increasing 2.6, 4.0, 11.4, 12.1 and 13.6 times, respectively, after 10 min treatment at 70° C.

And, as shown in FIG. 2, the residual enzyme activity of wild-type glucose oxidase GOD was 4.5 U/mg, and the residual enzyme activities of GOD-M1, GOD-M2, GOD-M3, GOD-M4 and GOD-M5 were 23.6 U/mg, 35.5 U/mg, 98.6 U/mg, 117.2 U/mg, 137.0 U/mg, respectively, increasing 4.2, 6.9, 20.9, 25.0 and 29.4 times, respectively, after treatment at 80° C. for 2 min.

The invention claimed is:

1. A glucose oxidase (GOD) mutant, having the amino acid sequence of SEQ ID NO: 3, SEQ ID NO: 4, SEQ ID NO: 5 or SEQ ID NO: 6.

2. A glucose oxidase (GOD) mutant gene encoding the glucose oxidase (GOD) mutant of claim 1.

3. A recombinant expression vector comprising the glucose oxidase (GOD) mutant gene of claim 2.

4. A recombinant host cell comprising the glucose oxidase (GOD) mutant gene of claim 2.

5. A method for preparing the glucose oxidase (GOD) mutant of claim 1, including the steps of transforming a host cell with a recombinant vector comprising a glucose oxidase (GOD) mutant gene to obtain a transformed host; culturing the obtained transformed host cell to induce the expression of the glucose oxidase (GOD) mutant; and recovering and purifying the glucose oxidase (GOD) mutant.

6. A method of converting β-D-glucose into gluconolactone, comprising contacting said β-D-glucose with the glucose oxidase (GOD) mutant of claim 1.

7. The glucose oxidase (GOD) mutant according to claim 1, being prepared by the following step:
transforming a host cell with a recombinant vector comprising a gene encoding said glucose oxidase (GOD) mutant to obtain a recombinant strain;
culturing the obtained recombinant strain to induce the expression of glucose oxidase (GOD) mutant; and
recovering and purifying the glucose oxidase (GOD) mutant.

* * * * *